US00PP21992P2

(12) United States Plant Patent
Fick

(10) Patent No.: US PP21,992 P2
(45) Date of Patent: Jun. 28, 2011

(54) ***ARCTOTIS* PLANT NAMED 'ON THE RED'**

(50) Latin Name: *Arctotis acaulis*
Varietal Denomination: On The Red

(76) Inventor: Paul Fick, George (ZA)

( * ) Notice: Subject to any disclaimer, the term of this patent is extended or adjusted under 35 U.S.C. 154(b) by 0 days.

(21) Appl. No.: 12/798,799

(22) Filed: Apr. 12, 2010

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of *Arctotis,* 'On The Red', characterized by its compact and dense growth habit, its strong and short flowering stems, its large number of ray florets, its continuous blooming habit, and its dark red ray florets with a yellow base creating a ring of yellow near the center of the inflorescences.

2 Drawing Sheets

Botanical classification: *Arctotis acaulis.*
Variety denomination: 'On The Red'.

BACKGROUND OF THE INVENTION

The present invention relates to a new and distinct cultivar of *Arctotis acaulis* and will be referred to hereafter by its cultivar name, 'On The Red'. 'On The Red' represents a new herbaceous perennial grown for container and landscape use.

The new cultivar, 'On The Red', was discovered as a whole plant mutation in a nursery plot by the Inventor in George, South Africa in spring of 2006. The nursery plot was planted with various unpatented cultivars and unnamed plants of *Arctotis acaulis* that were being evaluated for breeding potential. 'On The Red' arose as a seedling from open pollination and the parentage is unknown.

Asexual reproduction of the new cultivar was first accomplished by stem cuttings by the Inventor in 2007 in George, South Africa. Propagation by stem cutting and in vitro propagation has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'On The Red' as a unique cultivar of *Arctotis.*

1. 'On The Red' exhibits a compact growth habit with sturdy, well-branched stems and dense foliage.
2. 'On The Red' exhibits a floriferous blooming habit, continuously producing flowers during the growing season.
3. 'On The Red' exhibits inflorescences with a large number of ray florets.
4. 'On The Red' exhibits flowering stems that are short in height.
5. 'On The Red' exhibits inflorescences with ray florets that are dark red in color with a yellow base creating an inner yellow ring in the center of the inflorescence.

The new *Arctotis* is unique in comparison to other species and cultivars of *Arctotis* known to the Inventor. 'On The Red' differs from the selections in the research plot in having shorter flowering stems, a more compact growth habit, a larger number of ray florets, and in having dark red ray florets. 'On The Red' can be most closely compared to the cultivars 'Sunset Radiance' and 'Radiance Red' (both unpatented). They are both similar to 'On The Red' in leaf color and flower type. However, they both differ from 'On The Red' in having less compact growth habits, longer flowering stems, and fewer ray florets per bloom. In addition, 'Sunset Radiance' differs in having ray florets that are orange in color and 'Radiance Red' differs in having ray florets that are lighter red in color.

BRIEF DESCRIPTION OF THE DRAWINGS

The accompanying colored photographs illustrate the overall appearance and distinct characteristics of the new *Arctotis*. The plants in the photographs depict one year-old plants of 'On The Red' as grown in a greenhouse in one-gallon containers in Grand Saline, Tex.

The photograph in FIG. 1 illustrates the inflorescences, inflorescence buds and strong stems of 'On The Red'.

BOTANICAL DESCRIPTION OF THE PLANT

Figure 1:
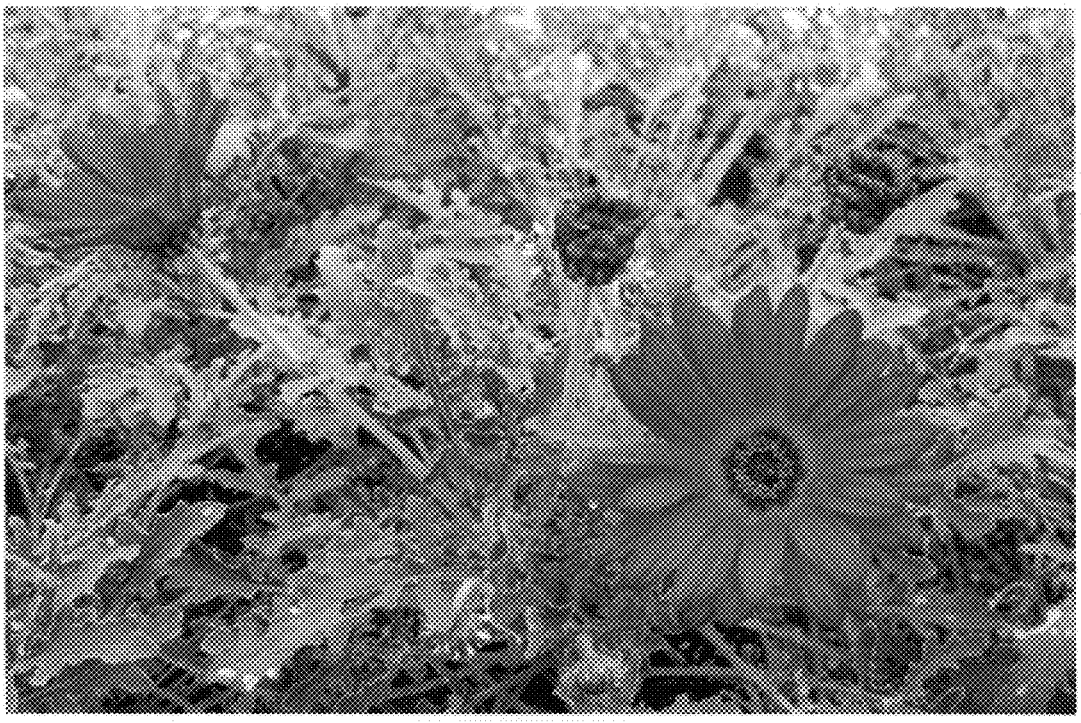
Figure 2:
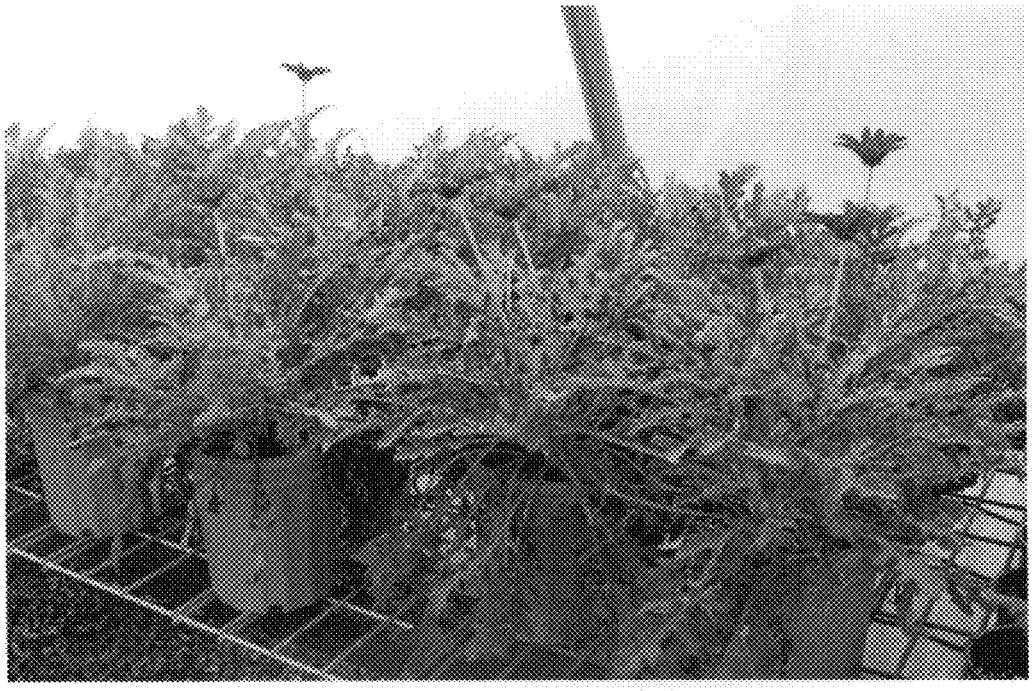
FIG. 2 provides a view of numerous plants of 'On The Red' plants and illustrates its compact growth habit.
Figure 3:
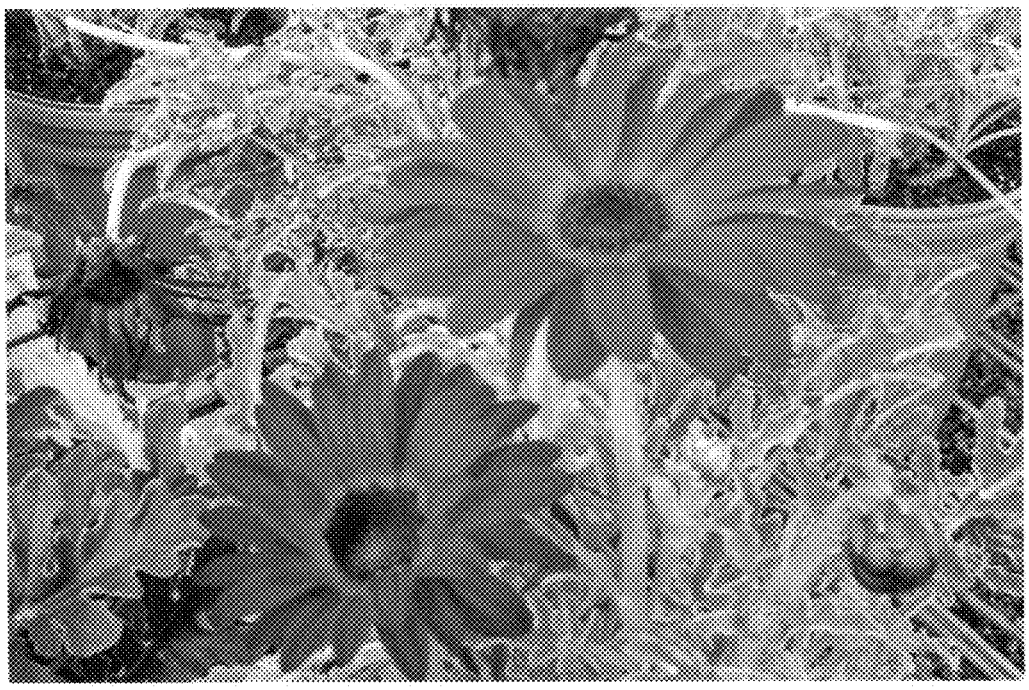
FIG. 3 provides a close-up view of the inflorescences of 'On The Red'. The colors in the photographs may differ slightly from the color values cited in the detailed botanical description, which accurately describe the colors of the new *Arctotis.*

The following is a detailed description of nine month-old plants of the new cultivar as grown in a greenhouse in one-gallon containers in Grand Saline, Tex. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming period.*—Blooms continuously from late winter into summer.

*Plant type.*—Herbaceous perennial, often grown as an annual.

*Plant habit.*—Compact, upright and mounded, freely branching.

*Height and spread.*—Up to 17.8 cm in height about 35.6 cm in width.

*Diseases and pests.*—No susceptibility or resistance to diseases or pests has been observed.

*Root description.*—Fibrous roots; freely branched, dense.

*Growth rate.*—Vigorous.

*Propagation.*—Stem cutting and tissue culture.

Stem description:

*Shape.*—Round, solid.

*Stem color.*—196C.

*Stem size.*—18.8 cm in length and 6 mm in diameter.

*Stem surface.*—Pubescent with fine hairs about 0.5 mm in length.

*Stem number.*—About 12 per one-gallon container.

*Internode length.*—5 to 7 mm in length.

*Stem strength.*—Strong.

*Branching.*—Multiple basal branches, up to 2 lateral branches per stem.

Foliage description:

*Leaf arrangement.*—Alternate.

*Leaf division.*—Simple.

*Leaf attachment.*—Petiolate.

*Leaf size.*—Up to 24 cm in length and 7 cm in width.

*Leaf shape.*—Lyrate-spatulate.

*Leaf apex.*—Broadly acute.

*Leaf base.*—Attenuate.

*Leaf margins.*—Irregularly serrated with deeply incised lobes.

*Leaf surface.*—Upper surface pubescent, lower surface tomentose.

*Leaf venation.*—Pinnate, arcuate, color upper surface 1440, color lower surface 193A.

*Leaf color.*—Newly formed upper surface; 137B, newly formed lower surface; 198D, fully expanded upper surface 147A, fully expanded lower surface 191C.

*Petioles.*—Average 7.6 cm in length, 2 mm in diameter, pubescent surface, upper surface 147C in color, lower surface 147D in color.

Inflorescence description:

*Type.*—Capitulum, heterogamous with ligulate ray florets around the head margin and disk florets in the center, forming a radiant head, disc and ray florets arranged acropetally on capitulum.

*Appearance.*—Inflorescences borne on terminal and axillary peduncles above foliage.

*Capitulum number.*—Average 20 inflorescences per plant.

*Lastingness of inflorescence.*—About 3 to 4 days; inflorescences persistent.

*Capitulum size.*—Matures to about 3.5 to 4 cm in depth and 5.5 to 6 cm in diameter, disk size is about 1.7 cm in diameter, receptacle is 1.5 cm in height and 1.6 cm in diameter.

*Fragrance.*—None detected.

*Phyllaries.*—About 40 arranged in 4 overlapping whorls, about 9 to 11 mm in length and 4 to 5 mm in width, oblong in shape, obtuse apex, truncate base, entire margin, pubescent upper surface 144A in color, smooth and glabrous lower surface 145A in color.

*Buds.*—Globose in shape, an average of 1.3 cm in depth and 1.5 cm in diameter, 187A to 187B in color.

*Peduncle.*—Strong, flexible, mostly erect, pubescent surface, typically 19.1 cm in length and 3 mm in diameter, 148C in color.

*Ray florets* (*sterile*).—Average 31, arranged in a double whorl, ligulate in shape, initially held upright becoming perpendicular to the peduncle, reflexed apices, about 2.7 cm in length and 9 mm in width, acute apex and base, entire margin, smooth and glabrous surface, velvety texture, color of upper surface when opening; 46B, color of lower surface when opening; 28C, color when fully opened upper surface; 4.6A and 28B towards the base, color lower surface when fully open; 39B with longitudinal stripes a blend of 46A and 46B.

*Disk florets* (*bisexual*).—Numerous, about 108, tubular in shape, massed at center of receptacle, about 6 to 7 mm in length and 2 mm in width at apex and 1 mm at base, immature floret 200D in color at apex, 164B in mid-section and 159C at base, mature floret N92 in color at apex, 161A in mid-section and 155C at base.

Reproductive organs (present on disk florets only):

*Gynoecium.*—Pistil; 1, 6 mm in length and 4 mm in width, style; 0.3 mm in width and 4 mm in length, color 155A becoming N77B towards apex, surrounded by stamens, stigma; bifid, each arm is reflexed, about 2.5 mm in length and N77B in color, ovary; inferior, single-celled, 0.4 mm in diameter and 155A in color.

*Androcoecium.*—Stamens; 5, fused, form a cylinder around style, 5 mm in length and 0.7 mm in width, dehisced longitudinally, 200A in color filaments; 1.5 mm in length, 0.5 m in width, 155C in color, pollen; abundant and 13A in color.

*Fruit.*—Not observed.

It is claimed:

1. A new and distinct cultivar of *Arctotis* plant named 'On The Red' substantially as herein illustrated and described.

* * * * *